(12) United States Patent
Huang et al.

(10) Patent No.: US 7,902,384 B2
(45) Date of Patent: Mar. 8, 2011

(54) ESTROGENIC-ACTIVE COMPOUNDS AND APPLICATION THEREOF

(75) Inventors: Ching-Jang Huang, Taipei (TW);
Ssu-Ching Wang, Taipei (TW);
Yueh-Hsiung Kuo, Taichung (TW);
Yong-Han Hong, Taipei (TW); Bi-Fong Lin, Taipei (TW); Chin Hsu, Taipei (TW)

(73) Assignee: National Taiwan University, Taipei (TW)

( * ) Notice: Subject to any disclaimer, the term of this patent is extended or adjusted under 35 U.S.C. 154(b) by 25 days.

(21) Appl. No.: 12/418,490

(22) Filed: Apr. 3, 2009

(65) Prior Publication Data
US 2010/0125102 A1    May 20, 2010

(30) Foreign Application Priority Data
Nov. 17, 2008   (TW) ................................ 97144382 A

(51) Int. Cl.
*C07D 315/00*    (2006.01)
(52) U.S. Cl. ....................................................... 549/417
(58) Field of Classification Search .................... 549/417
See application file for complete search history.

(56) References Cited

U.S. PATENT DOCUMENTS
5,292,898 A * 3/1994 Hammann et al. ............ 549/292

OTHER PUBLICATIONS

Kuo et al. STN Accession No. 2002, Document No. 138:86521, Abstract of Journal of the Chinese Chemical Society (Taipei, Taiwan) (2002), 49(3),427-431.*

* cited by examiner

*Primary Examiner* — Nizal S Chandrakumar
(74) *Attorney, Agent, or Firm* — WPAT, P.C.; Anthony King

(57) ABSTRACT

The present invention relates to compounds having estrogenic activity selected from the group consisting of Loliolide, (4S,6S)-4-Hydroxy-6-nonadecyl-tetrahydro-pyran-2-one, (4R,6S)-4-Hydroxy-6-nonadecyl-tetrahydro-pyran-2-one and analogues thereof. The compounds of the present invention are selective estrogen receptor modulator, which can selectively activate ERβ and simultaneously express high estrogenic activity, and also can be applied as medical or food compositions to improve estrogen deficiency-related symptoms.

9 Claims, 6 Drawing Sheets

ESTROGENIC-ACTIVE COMPOUNDS AND APPLICATION THEREOF

BACKGROUND OF THE INVENTION

1. Field of the Invention

The present invention relates to compounds containing estrogenic activity, and in particular to compounds isolated from plants and containing estrogenic activity.

2. The Prior Arts

More than half of the women who faced menopause have estrogen-deficiency related syndromes due to ovary atrophy. The symptoms include heart, blood vessel, metabolic and mentally diseases, as well as heat flush, sweats, rapid heart beat and so on. Therefore, hormone replacement therapy (HRT) was carried out in menopause women to prevent menopausal symptoms due to insufficient estrogen recently.

However, an increased association of estrogen-only HRT with endometrioid ovarian cancer was revealed in previous reports. The combination of conjugated equine estrogens (CEE) and progesterone such as medroxyprogesterone acetate (MPA) was suggested at present to prevent the chance of endometrioid ovarian cancer induced by estrogen-only HRT. However, a study of USA in 2002 showed that women in the CEE plus MPA group had higher risks of breast cancer (26%), stroke (41%), cardio disease (29%), and venous thromboembolism (113%). There were indications of health damages and side effects for those receiving therapy. Therefore, physicians were forced to search for alternative treatments. These alternatives include non-hormone chemicals, such as clonidine, venlafaxine, fluoxetine, and paroxetine, which were not only less efficient than HRT in treating menopausal symptoms, but also induced annoying side effects.

It was known from the studies of molecular biology that estrogens operate in cells through the binding of estrogen receptors (ER) to initiate the gene expression. These estrogen regulatory genes contain estrogen responsive element (ERE) in the promoter region to present their activities. A compound that binds to the ER and produces partial estrogenic effects is a partial agonist, such as diethylstilbestrol (DES). Conversely, a compound that binds to the ER and blocks binding of estrogens but does not allow the receptor to adopt a functionally active state is the to be an antagonist or an antiestrogen, such as tamoxifen, which shows inhibitory effect on estrogen-dependent cancer. There are two types of ERs, ERα and ERβ, being identified in quite different regions. ERα expression is primarily found in the endometrium and breast and uterus. In contrast, ERβ is found mainly in brain, bone and so on. Ideal selective estrogen receptor modulators (SERMs) are ER ligands that act like estrogens in tissues of blood vessels and bones, but act weakly in mammary gland. These molecules would be of great beneficial effect in menopause women.

Therefore, development of an estrogen alternative for menopause women to improve the symptoms but without side effects related to estrogens purified from animals (such as CEE) or non-hormone therapy is in urgent need.

SUMMARY OF THE INVENTION

In order to solve the abovementioned problems, the present invention isolated compounds containing estrogenic activity from alfalfa extract that are selected from the group consisting of Loliolide, (4S,6S)-4-Hydroxy-6-nonadecyl-tetrahydro-pyran-2-one, (4R,6S)-4-Hydroxy-6-nonadecyl-tetrahydro-pyran-2-one and analogues thereof.

The chemical structure of Loliolide in the present invention was shown in formula (1), with a molecular formula of $C_{11}H_{16}O_3$, and molecular weight of 196.25.

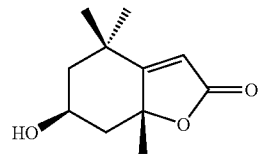

(1)

The chemical structure of (4S,6S)-4-Hydroxy-6-nonadecyl-tetrahydro-pyran-2-one in the present invention was shown in formula (2), wherein n=0, 1, 2, 3 . . . , or 16. A preferred compound of the general formula (2) is (4S,6S)-4-Hydroxy-6-nonadecyl-tetrahydro-pyran-2-one when n=16, with a molecular formula of $C_{24}H_{46}O_3$ and molecular weight of 382.63.

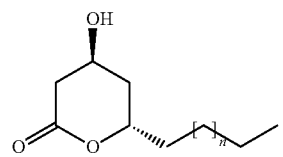

(2)

The chemical structure of (4R,6S)-4-Hydroxy-6-nonadecyl-tetrahydro-pyran-2-one in the present invention was shown in formula (3), wherein n=0, 1, 2, 3 . . . , or 16. A preferred compound of the general formula (3) is (4R,6S)-4-Hydroxy-6-nonadecyl-tetrahydro-pyran-2-one when n=16, with a molecular formula of $C_{24}H_{46}O_3$ and molecular weight of 382.63.

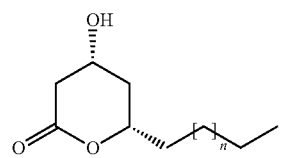

(3)

The compounds containing estrogenic activity of the present invention can be synthesized from conventional organic chemistry, or extracted and purified from nature plants (such as alfalfa), but is not limited to.

The compounds containing estrogenic activity of the present invention activate both ERα and ERβ, and express superior estrogenic activity.

The present invention also provides a pharmaceutical composition for treating estrogen-deficiency related syndromes, which comprises an effective amount of the compound, or further comprises a pharmaceutically accepted carrier.

The present invention also provides a food composition for improving estrogen-deficiency related syndromes, which comprises an effective amount of the compound, or further comprises a food additive. The food additive is a dietary supplement, a food material or a combination of the dietary supplement and the food material. The estrogen-deficiency related syndromes include, but are not limited to, dry skin, voluntary urination, heat flush, night sweat, insomnia and others as well as bone loss.

The present invention is further explained in the following embodiment illustration and examples. Those examples below should not, however, be considered to limit the scope of the invention, it is contemplated that modifications will readily occur to those skilled in the art, which modifications will be within the spirit of the invention and the scope of the appended claims.

DETAILED DESCRIPTION OF THE PREFERRED EMBODIMENT

Figure 1:
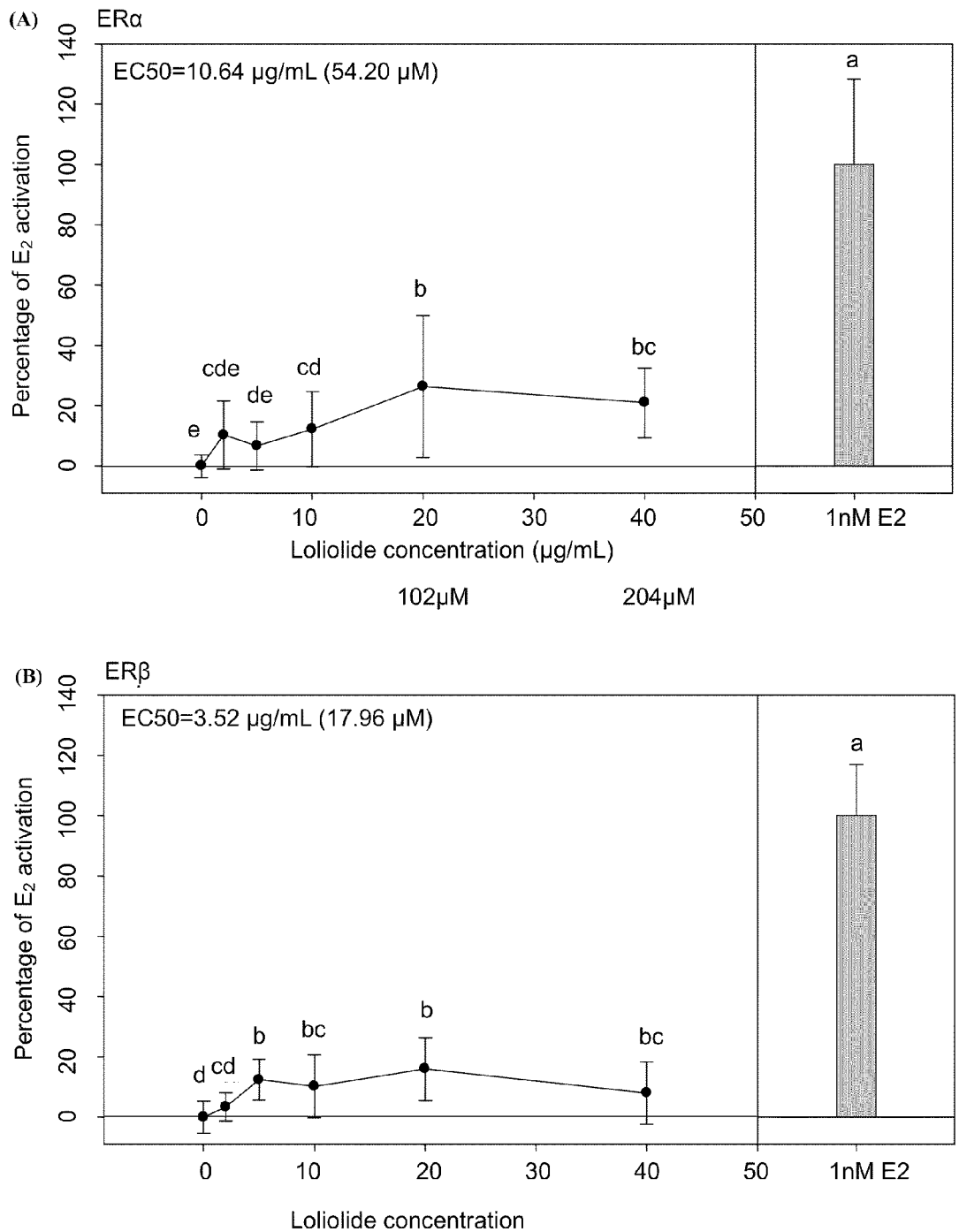
FIG. 1 shows the dose response curve of (A) GAL4-hERα and (B) GAL4-hERβ in the presence of various concentration of Loliolide in one embodiment of the present invention.

First, a method for assessing the estrogenic activity in the field samples was established. This method comprises: preparing a cell line transfected with plasmids which can screen estrogenic activity substances. Samples to be assayed were added into the culture medium when cultivating the cell line and 17β-estradiol ($E_2$) was added in the positive control group. The reporter gene in the plasmid was expressed when the sample to be assayed contains estrogenic activity. Among them, the samples to be assayed in the examples of the invention include Loliolide, (4S,6S)-4-Hydroxy-6-nonadecyl-tetrahydro-pyran-2-one, (4R,6S)-4-Hydroxy-6-nonadecyl-tetrahydro-pyran-2-one. The expression levels of the reporter gene in the following examples revealed estrogenic activities of these samples. Further more, the assessing method established in this invention was shown to effectively and precisely assess the estrogenic activity the samples to be assayed when compared to the estrogenic activity induced by 17β-estradiol. The details of establishing the assessing method are described as follows:

EXAMPLE 1

Method for Assessing the Estrogenic Activity

Plasmid pBKCMV containing GAL4hERα (or ERβ) ligand binding domain (LBD) chimeric receptors and plasmid containing $(UAS)_4$-alkaline phosphatase (ALP) reporter gene were co-transfected into Chinese hamster cells (CHO-k1). Compounds with estrogenic activity would interact with estrogen-specific ER to induce the binding of GAL4 and upstream activation sequence (UAS) specifically to initiate the expression of ALP gene. Therefore, the ALP activity can be used to determine whether the samples to be assayed have the estrogenic activity.

1. Cell Culture and Transfection

The CHO-k1 purchased from the Food Industry Research and Development Institute with an accession number of CCRC 60006 were cultivated with medium containing 10% FBS and Ham's F12 nutrient mixture (GIBCOBRL® 11765-054). Cells in high confluence were plated onto 96-well culture plate the day before transfection. The plate was then washed to remove the serum during the day of transfection, followed by addition of two plasmid DNA, GAL4-hERα and $(UAS)_4$-ALP in the ratio of 5:1, or GAL4-hERβ and $(UAS)_4$-ALP in the ratio of 4:1, together with Lipofectamine™ 2000 transfection agent and culture medium to form DNA-liposome complex for 5 h.

2. Estrogenic Activity Assay

The sample to be assayed was added into the medium of transfected cells and cultivated for 2 days. The medium was aliquoted for ALP assay using 4-Nitrophenyl phosphate disodium salt hexahydrate (pNPP) as the colorimetric substrate for alkaline phosphatase, and reading the absorbance of 405 nm. The known ER activator $E_2$ at the concentration of 1 nM was used as the positive control.

$E_2$ and Genistein were used to confirm the effectiveness of this assay. It was shown that APL activity was increased with the addition of $E_2$, and the $EC_{50}$ (ligand concentration yielding half-maximal activation) values of ERα and ERβ were $1 \times 10^{-1}$ nM and $5 \times 10^{-2}$ nM, respectively. While $EC_{50}$ values of ERα and ERβ resulted in 242.57 nM and 6.72 nM respectively after addition of Genistein. Genistein showed a much lower effective concentration for ERβ than for ERα. Therefore, the estrogenic activity assay determined by transcription of reporter gene can be used in screening selective estrogen receptor modulators (SERMs).

EXAMPLE 2

Purification of Compounds Containing Estrogenic Activities from Alfalfa

Forty volumes of ethyl acetate (EA) were added into one and half kg of alfalfa frozen powder in batches of 100 g and stirred at room temperature overnight. The solution was filtered for vacuum assisted fast filtration (with filters of Whatman No. 2) twice and the filtrates were collected and evaporated by an evaporator at 45-50° C. to a concentrate as the alfalfa extract.

The filtrate of alfalfa was dissolved in EA and added with 1.5 fold of silica gel (230-400 mesh) for absorption, followed by chromatography analysis with 15 volumes of silica gel (20-230 mesh). The mobile phase consisted of 1-hexane and EA at different ratio, with the gradient conditions starting from 100% 1-hexane to 100% EA, followed by adding methanol (to increase the polarity of mobile phase) to 20% methanol/EA. Proper amount of column effluent was collected as a fraction. Each fraction was evaporated to remove the solvent. These fractions were analyzed with thin layer chromatography (TLC). The fractions from each polar region were dissolved in absolute ethanol, which were subjected to estrogenic activity assay and NMR analysis to determine the primary structure and purity.

The alfalfa extracts obtained after abovementioned silica gel chromatography and estrogenic activity assay were then subjected to High Performance Liquid chromatography (HPLC) for purification and isolation. The separation was performed on a Phenomenex Luna 5μ Silica (10 mm×250 mm) column, and detected with a RID-10A Shiniadzu Refractive Index Detector. The potent fractions with estrogenic activity were analyzed for the composition with a NMR and mass. The EA extracts of alfalfa obtained from different elution condition and their estrogenic activity were described respectively below (FIGS. 1-6). In addition, 17β-estradiol was co-added with these compounds into the cells as described in Example 1 to mimic the peri-menopause condition (normal estrogen concentration) for assessment of possible antagonism or synergistic agonism between 17β-estradiol and compounds, while single sample addition was used to mimic the condition of menopause women (lacking estrogen).

Figure 2:
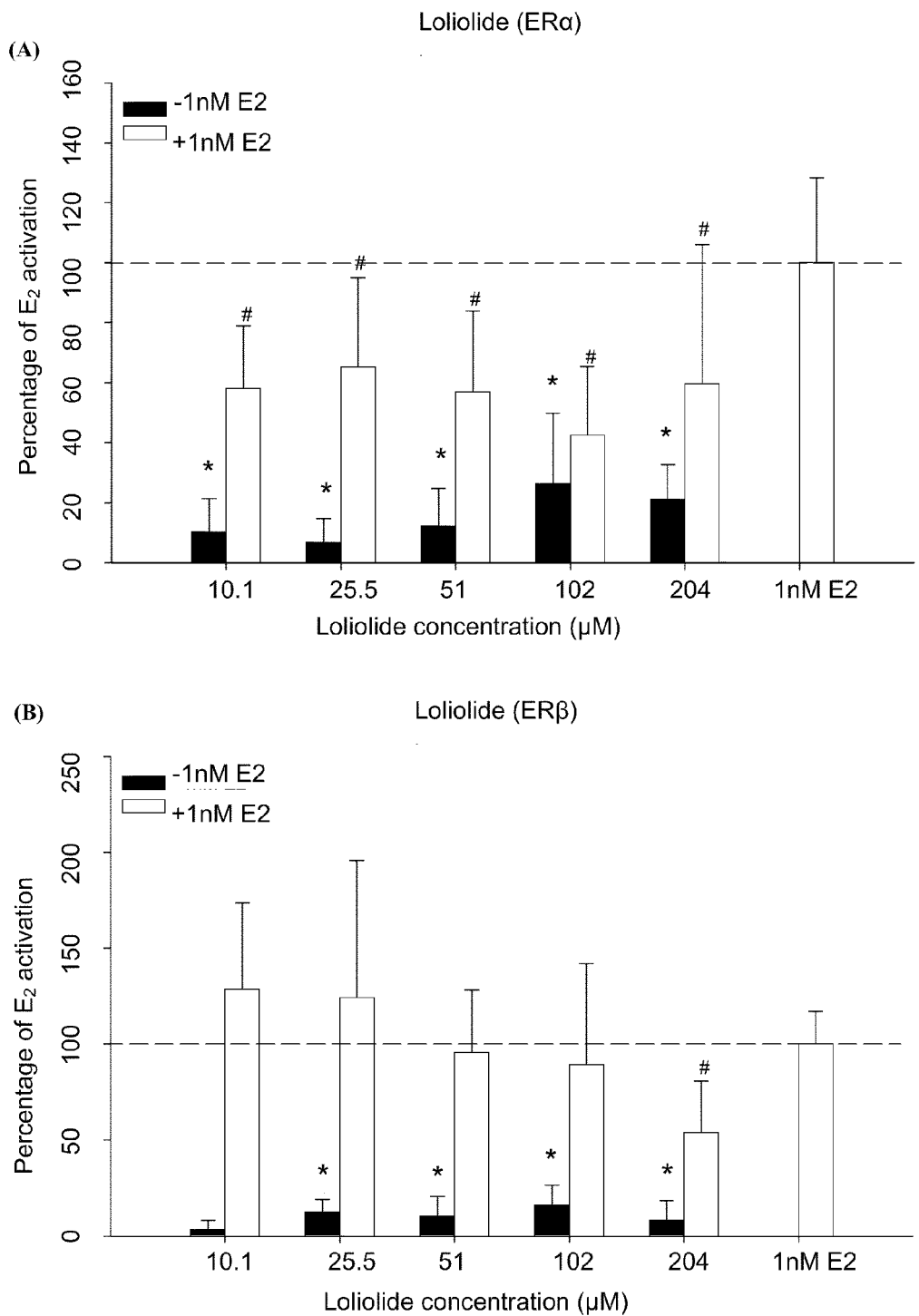
FIG. 2 shows the dose response curve of (A) GAL4-hERα and (B) GAL4-hERβ after co-administrated with Loliolide and 1 nM of 17β-estradiol ($E_2$) in one embodiment of the present invention.
Figure 3:
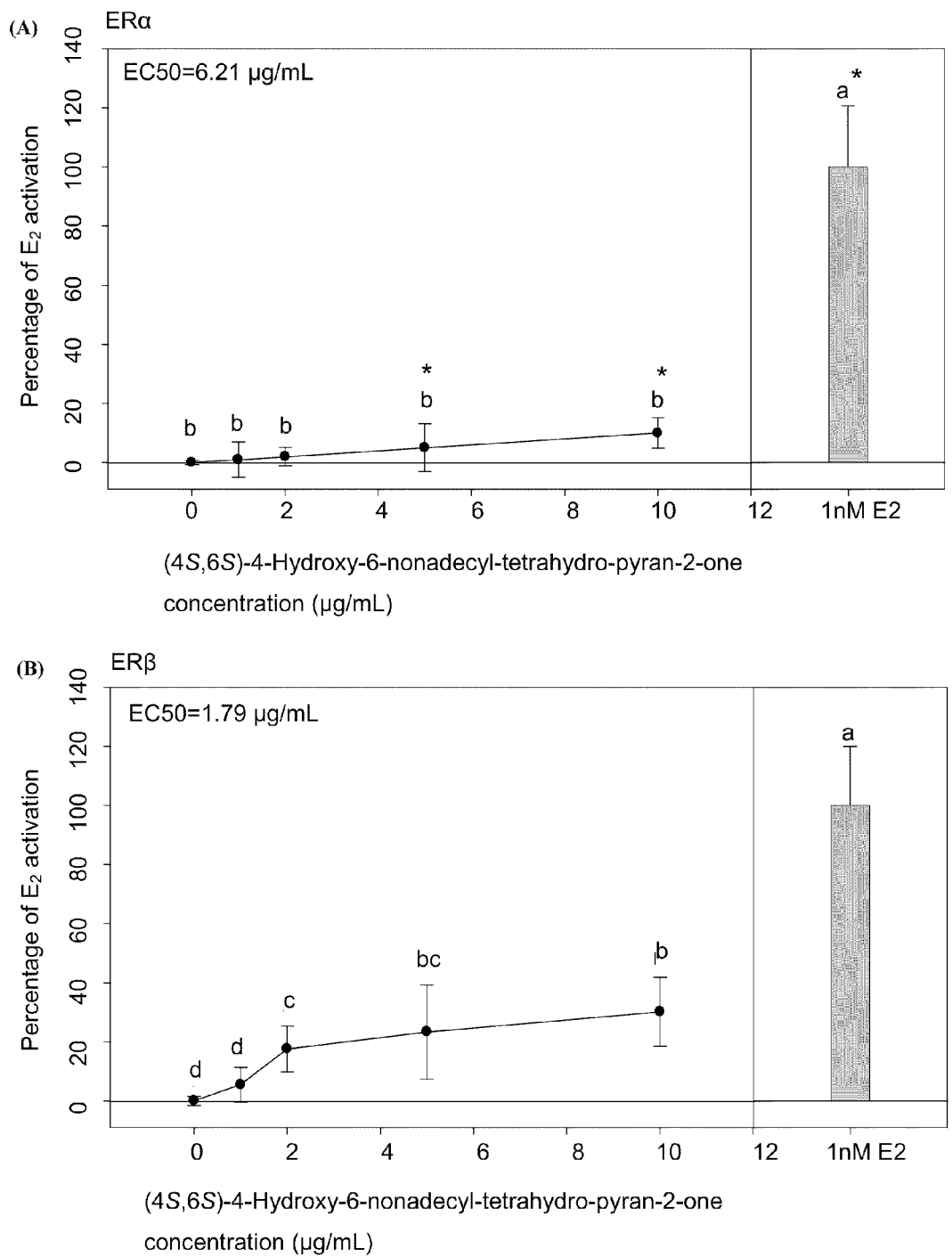
FIG. 3 shows the dose response curve of (A) GAL4-hERα and (B) GAL4-hERβ in the presence of various concentration of (4S,6S)-4-Hydroxy-6-nonadecyl-tetrahydro-pyran-2-one in one embodiment of the present invention.
Figure 4:
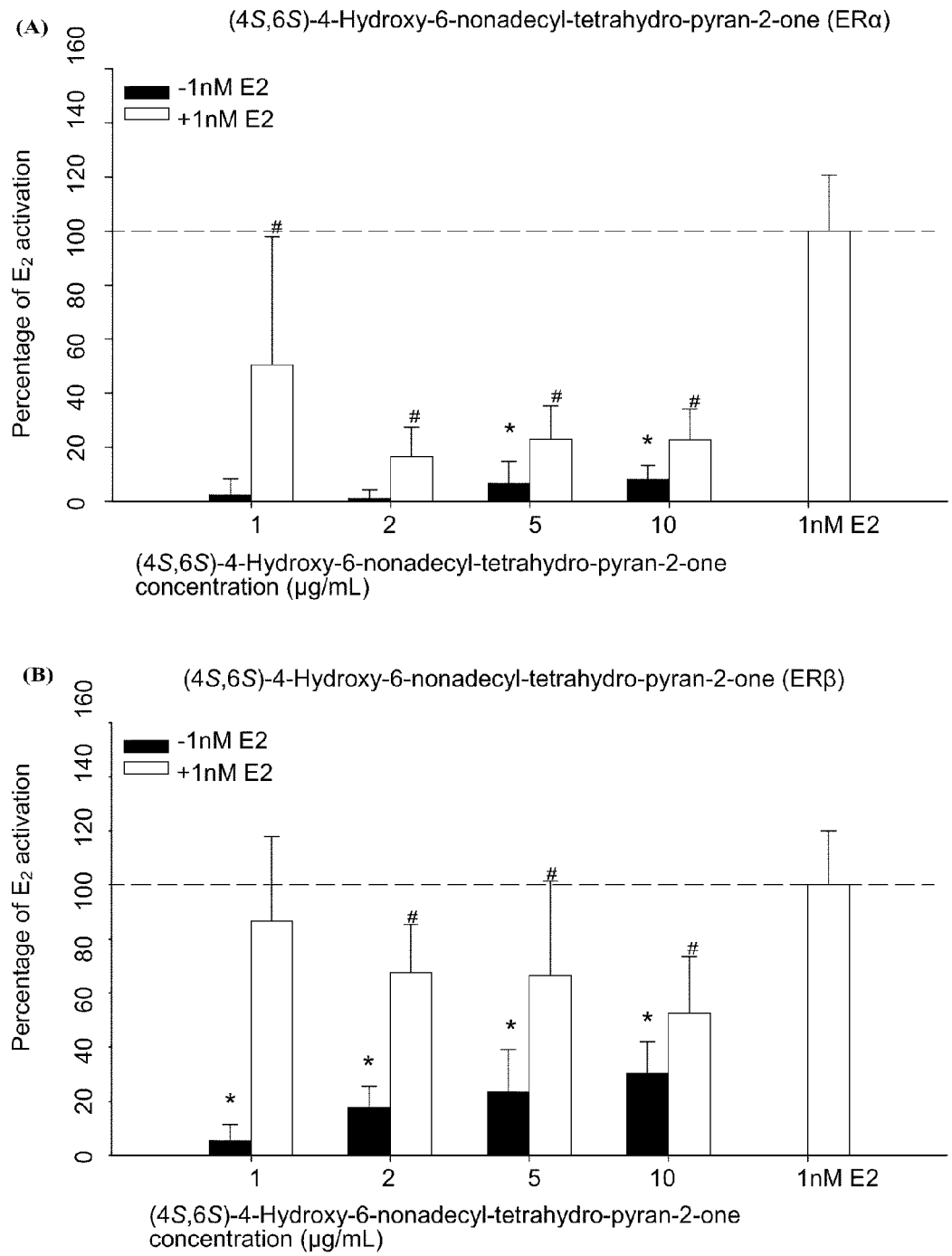
FIG. 4 shows the dose response curve of (A) GAL4-hERα and (B) GAL4-hERβ after co-administrated with (4S,6S)-4-Hydroxy-6-nonadecyl-tetrahydro-pyran-2-one and 1 nM of 17β-estradiol ($E_2$) in one embodiment of the present invention.
Figure 5:
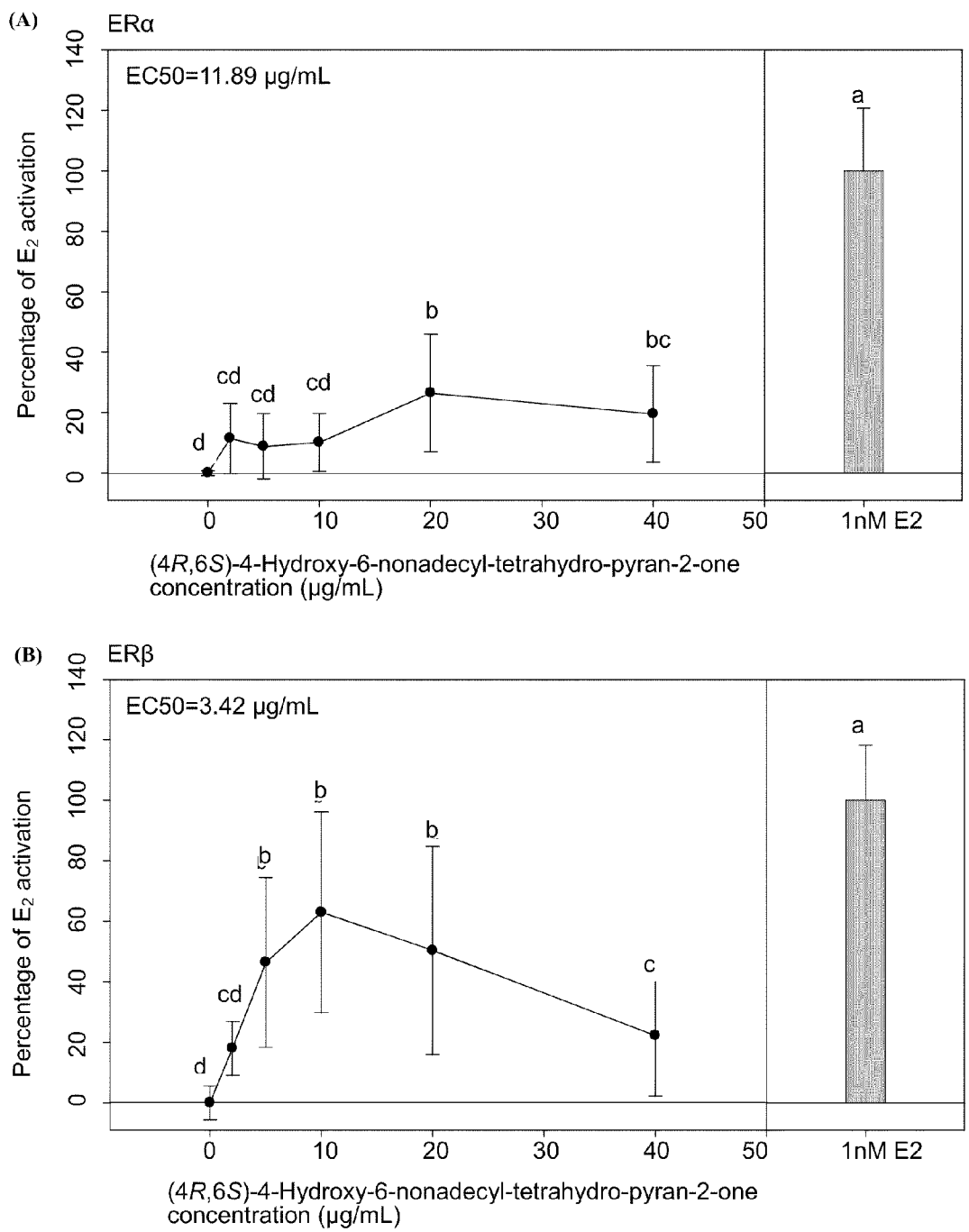
FIG. 5 shows the dose response curve of (A) GAL4-hERα and (B) GAL4-hERβ in the presence of various concentration of (4R,6S)-4-Hydroxy-6-nonadecyl-tetrahydro-pyran-2-one in one embodiment of the present invention.

The results on FIG. 1, FIG. 3, and FIG. 5 were represented as means±SD (standard deviation) of triplicate independent experiments. Single addition of 17β-estradiol (E2) in the concentration of 1 nM was set as the positive control. Various English alphabet labeling represents values that are significant different with others on complete randomized design (p<0.05). The results on FIG. 2, FIG. 4, and FIG. 6 were represented as means±SD (standard deviation) of triplicate independent experiments. Single addition of 17β-estradiol ($E_2$) in the concentration of 1 nM was set as the positive control. E2 co-addition was shown by blank bars and those without E2 addition was shown in filled bars. * and # labels represented significant difference after t-test (p<0.05) with no E2 or addition of E2 respectively.

1. Loliolide
(1) Purification of Compound

Once and half liters of the 30% EA/70% hexane elution solution from alfalfa EA extracts after abovementioned silica gel chromatography were collected, followed by collection of one liter of the 50% EA/50% hexane elution solution. The fractions were concentrated through reduced pressure evaporation and further purified by repeated silica gel chromatography using 20% EA/80% hexane (including partial of the 30% EA/70% hexane eluent) as eluent. This solution was separated by HPLC with mobile phase of 45% EA/45% dichloromethane/10% Hex at flow rate of 4 ml/min. The eluent collected at 18.8 min to 20.6 min was separated again by HPLC with mobile phase of 55% EA/45% Hex at flow rate of 4 ml/min. The eluent at 23.6 min to 25.4 min was collected and analyzed with a hydrogen based NMR for the chemical structure.

The chemical structure of this eluent was determined to be Loliolide in this invention as shown in formula (1), which has a molecular formula of $C_{11}H_{16}O_3$, and a molecular weight of 196.25.

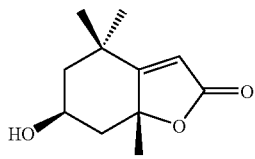

(1)

(2) Estrogenic Activity of the Compound

Various concentrations of Loliolide of formula (1) were used to treat the cells in Example 1. The estrogenic activity of Loliolide was shown in FIG. 1. In addition, 1 nM of 17β-estradiol was co-added with the compound into the cells as described in Example 1 to test for antagonism or synergistic agonism (FIG. 2).

Referring to FIG. 1, the estrogenic activities were shown with the treatment of Loliolide. The ALP activities were enhanced with the increase of Loliolide concentration in a dose-dependent manner. The maximal activation of the estrogenic activity was achieved at the Loliolide concentration of 20 μg/ml (102.0 μM), and the $EC_{50}$ was 10.64 pg/ml (54.20 μM) for ERα, and 3.52 μg/ml (17.96 μM) for ERβ respectively. Loliolide was shown to have better activation efficiency in ERβ, which therefore can be used as selective estrogen receptor modulators (SERM) in menopause women.

Referring to FIG. 2, estrogenic activity was shown after 1 nM of 17β-estradiol was co-added with the Loliolide into the cells. The activation of ERα due to estrogen was significantly decreased by Loliolide at the concentration of 10.1 μM, and the activation of ERβ due to estrogen was significantly decreased by Loliolide at the concentration of 204 μM in comparison to single addition of estrogen. Therefore, Loliolide at specific concentration was shown to have antagonistic activity toward 17β-estradiol when co-existed with 17β-estradiol, which can be used as selective estrogen receptor modulators (SERM) to ERα in peri-menopause women.

2. (4S,6S)-4-Hydroxy-6-nonadecyl-tetrahydro-pyran-2-one
(1) Purification of (4S,6S)-4-Hydroxy-6-nonadecyl-tetrahydro-pyran-2-one Once and half liters of the 30% EA/70% hexane elution solution from alfalfa EA extracts after abovementioned silica gel chromatography were collected, followed by collection of one liter of the 50% EA/50% hexane elution solution. The fractions were concentrated through reduced pressure evaporation and further purified by repeated silica gel chromatography using 20% EA/80% hexane (including partial of the 30% EA/70% hexane eluent) as eluent. This solution was separated by HPLC with mobile phase of 45% EA/45% dichloromethane/10% Hex at flow rate of 4 ml/min. The eluent collected at 19 min to 21.5 min was separated again by HPLC with mobile phase of 55% EA/45% Hex at flow rate of 4 ml/min. The eluent at 27.5 min to 30 min was collected and analyzed with a hydrogen based NMR for the chemical structure. The chemical structure of this novel compound was determined to be (4S,6S)-4-Hydroxy-6-nonadecyl-tetrahydro-pyran-2-one as shown in formula (2), wherein n=0, 1, 2, 3 . . . , or 16. When n=16, the structure has a molecular formula of $C_{24}H_{46}O_3$, and a molecular weight of 382.63.

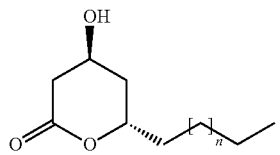

(2)

(2) Estrogenic Activity of (4S,6S)-4-Hydroxy-6-nonadecyl-tetrahydro-pyran-2-one

Various concentrations of (4S,6S)-4-Hydroxy-6-nonadecyl-tetrahydro-pyran-2-one in formula (2) were used to treat the cells in Example 1. The estrogenic activity of (4S,6S)-4-Hydroxy-6-nonadecyl-tetrahydro-pyran-2-one was shown in FIG. 3. In addition, 1 nM of 17β-estradiol was co-added with this compound into the cells as described in Example 1 to test for antagonism or synergistic agonism (FIG. 4).

Referring to FIG. 3, the estrogenic activities were shown with the treatment of (4S,6S)-4-Hydroxy-6-nonadecyl-tetrahydro-pyran-2-one in the invention. The ALP activities were enhanced with the increase of concentration of the compound in a dose-dependent manner. The maximal activation of the ERα and ERβ activity was achieved at the concentration of 10 μg/ml, and the $EC_{50}$ was 6.21 μg/ml for ERα, and 1.79 μg/ml for ERβ respectively. (4S,6S)-4-Hydroxy-6-nonadecyl-tetrahydro-pyran-2-one was shown to have better activation efficiency in ERβ, which therefore can be used as selective estrogen receptor modulators (SERM) in menopause women.

Referring to FIG. 4, estrogenic activity was shown after 1 nM of 17β-estradiol was co-added with (4S,6S)-4-Hydroxy-6-nonadecyl-tetrahydro-pyran-2-one into the cells. The activation of ERα due to estrogen was significantly decreased by (4S,6S)-4-Hydroxy-6-nonadecyl-tetrahydro-pyran-2-one at the concentration of 1 μg/ml, and the activation of ERβ due to estrogen was significantly decreased at the concentration of 2 μg/ml in comparison to single addition of estrogen. Therefore, (4S,6S)-4-Hydroxy-6-nonadecyl-tetrahydro-pyran-2-one at specific concentration was shown to have antagonistic activity toward 17β-estradiol when co-existed with 17β-estradiol, which can be used as selective estrogen receptor modulators (SERM) to ERα in peri-menopause women.

3. (4R,6S)-4-Hydroxy-6-nonadecyl-tetrahydro-pyran-2-one (1) Purification of (4R,6S)-4-Hydroxy-6-nonadecyl-tetrahydro-pyran-2-one Once and half liters of the 30% EA/70% hexane elution solution from alfalfa EA extracts after abovementioned silica gel chromatography were collected, followed by collection of one liter of the 50% EA/50% hexane elution solution. The fractions were concentrated through reduced pressure evaporation and further purified by repeated silica gel chromatography using 20% EA/80% hexane (including partial of the 30% EA/70% hexane eluent) as eluent. This solution was separated by HPLC with mobile phase of 45% EA/45% dichloromethane/10% Hex at flow rate of 4 ml/min. The eluent collected at 26.1 min to 30.5 min was separated again by HPLC with mobile phase of 55% EA/45% Hex at flow rate of 4 ml/min. The eluent at 23 min to 25 min was collected and analyzed with a hydrogen based NMR for the chemical structure. The chemical structure of this novel compound was determined to be (4R,6S)-4-Hydroxy-6-nonadecyl-tetrahydro-pyran-2-one as shown in formula (3), wherein n=0, 1, 2, 3 . . . , or 16. When n=16, the structure has a molecular formula of $C_{24}H_{46}O_3$, and a molecular weight of 382.63.

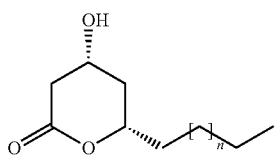

(3)

(2) Estrogenic Activity of (4R,6S)-4-Hydroxy-6-nonadecyl-tetrahydro-pyran-2-one

Various concentrations of (4R,6S)-4-Hydroxy-6-nonadecyl-tetrahydro-pyran-2-one in formula (3) were used to treat the cells in Example 1. The estrogenic activity of (4R,6S)-4-Hydroxy-6-nonadecyl-tetrahydro-pyran-2-one was shown in FIG. 5. In addition, 1 nM of 17β-estradiol was co-added with this compound into the cells as described in Example 1 to test for antagonism or synergistic agonism (FIG. 6).

Referring to FIG. 5, the estrogenic activities were shown with the treatment of (4R,6S)-4-Hydroxy-6-nonadecyl-tetrahydro-pyran-2-one in the invention. The ALP activities were enhanced with the increase of concentration of the compound in a dose-dependent manner. The maximal activation of the ERα and ERβ activity was achieved at the concentration of 20 μg/ml and 10 μg/ml respectively, and the $EC_{50}$ was 11.89 pg/ml for ERα, and 3.42 μg/ml for ERβ respectively. (4R,6S)-4-Hydroxy-6-nonadecyl-tetrahydro-pyran-2-one was shown to have better activation efficiency in ERβ, which therefore can be used as selective estrogen receptor modulators (SERM) in menopause women.

Figure 6:
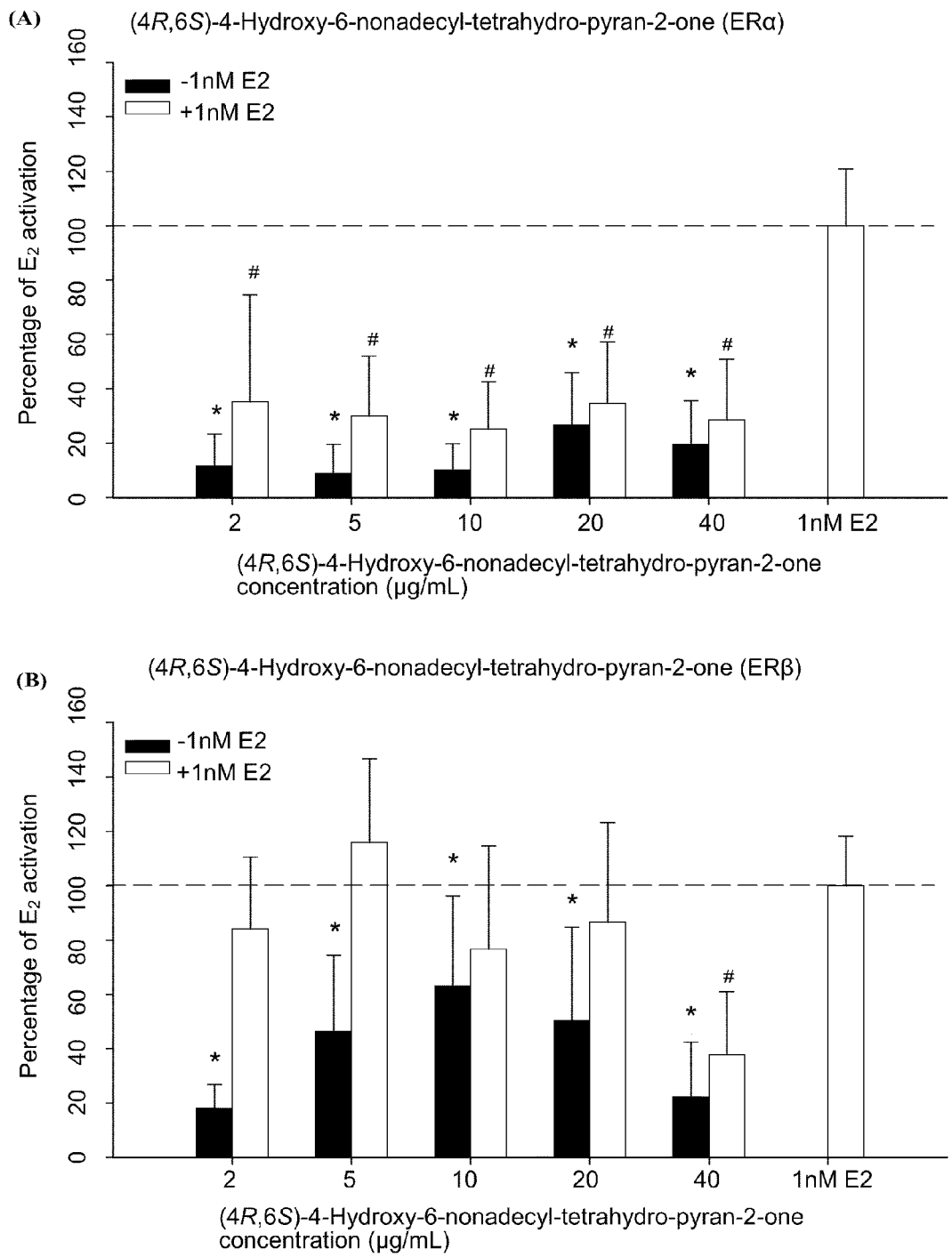
FIG. 6 shows the dose response curve of (A) GAL4-hERα and (B) GAL4-hERβ after co-administrated with (4R,6S)-4-Hydroxy-6-nonadecyl-tetrahydro-pyran-2-one and 1 nM of 17β-estradiol ($E_2$) in one embodiment of the present invention.

Referring to FIG. 6, estrogenic activity was shown after 1 nM of 17β-estradiol was co-added with (4R,6S)-4-Hydroxy-6-nonadecyl-tetrahydro-pyran-2-one into the cells. The activation of ERα due to estrogen was significantly decreased by (4R,6S)-4-Hydroxy-6-nonadecyl-tetrahydro-pyran-2-one at the concentration of 2 μg/ml, and the activation of ERβ due to estrogen was significantly decreased at the concentration of 2 μg/ml in comparison to single addition of estrogen. Therefore, (4R,6S)-4-Hydroxy-6-nonadecyl-tetrahydro-pyran-2-one at specific concentration was shown to have antagonistic activity toward 17β-estradiol when co-existed with 17β-estradiol, which can be used as selective estrogen receptor modulators (SERM) to ERα in peri-menopause women.

In summary, the compounds isolated and purified in the present invention which contain estrogenic activity were ideal SERM. They can selectively activate ERβ, and show excellent estrogenic activity. Therefore these compounds were postulated to act in cells of blood vessels and bone tissues but have weak activities toward cells of mammary glands or uterus to lower the morbidity of breast cancer, endometrial cancer, or other side effects. In addition, co-administration of these compounds with estrogen showed antagonistic activity toward estrogen, which can lower the side effects such as increasing morbidity of breast cancer and the like caused by single addition of estrogen.

Therefore the compound in the present invention can be used as alternatives or supplements for animal estrogen. For example, an effective amount of the compounds can be applied or further incorporated in a pharmaceutically acceptable carrier in the pharmaceutical compositions for improving the estrogen-deficiency related syndromes. In addition, the compounds in the present invention can also be applied in the food compositions for improving the estrogen-deficiency related syndromes. The food compositions can further comprises a food additive, which is a dietary supplement, a food material or a combination of the dietary supplement and the food material. The dietary supplement can be citrate, vitamin, pantothenate, niacin, or other healthy ingredients, and the food material can be, but is not limited to, vegetable, or meat.

pharmaceutical compositions or food compositions containing the compounds of the present invention can be used to improve the estrogen deficiency syndromes including, but not limited to, dry skin, voluntary urination, macular degeneration, heat flush, night sweat, insomnia and other estrogen deficiency syndromes as well as bone loss.

What is claimed is:

1. A compound of formula (2) or formula (3):

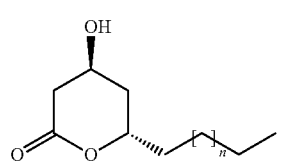

formula (2)

-continued

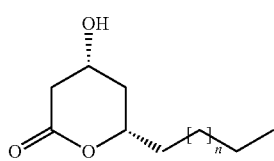
formula (3)

wherein n=16, the formula (2) is (4S,6S)-4-Hydroxy-6-nonadecyl-tetrahydro-pyran-2-one, and the formula (3) is (4R,6S)-4-Hydroxy-6-nonadecyl-tetrahydro-pyran-2-one.

2. The compound as claimed in claim 1, wherein the compound selectively activates estrogen receptor β (ERβ) in menopause women.

3. The compound as claimed in claim 1, wherein the compound reduces the activation of estrogen receptor α (ERα) induced by estrogen when co-administrated with estrogen.

4. A pharmaceutical composition for improving estrogen-deficiency related syndromes, which comprises an effective amount of a compound and a pharmaceutically acceptable carrier, wherein the compound is selected from the group consisting of formula (2), and formula (3):

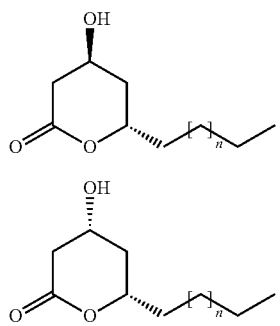

formula (2)

formula (3)

wherein n=16, the formula (2) is (4S,6S)-4-Hydroxy-6-nonadecyl-tetrahydro-pyran-2-one, and the formula (3) is (4R,6S)-4-Hydroxy-6-nonadecyl-tetrahydro-pyran-2-one.

5. The pharmaceutical composition as claimed in claim 4, wherein the compound selectively activates estrogen receptor β (ERβ) in menopause women.

6. The pharmaceutical composition as claimed in claim 4, wherein the compound reduces the activation of estrogen receptor α (ERα) induced by estrogen when co-administrated with estrogen.

7. A food composition for improving estrogen-deficiency related syndromes, which comprises a compound selected from the group consisting of formula (2), and formula (3):

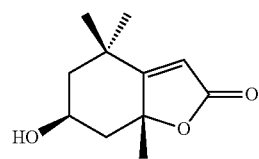
formula (1)

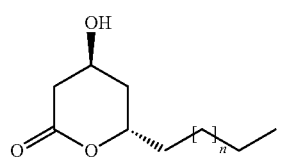
formula (2)

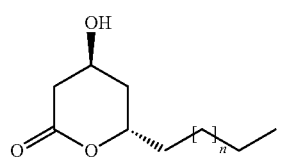
formula (3)

wherein n=16, the formula (2) is (4S,6S)-4-Hydroxy-6-nonadecyl-tetrahydro-pyran-2-one, and the formula (3) is (4R,6S)-4-Hydroxy-6-nonadecyl-tetrahydro-pyran-2-one.

8. The food composition as claimed in claim 7, wherein the food composition further comprises a food additive, which is a dietary supplement, a food material or a combination of the dietary supplement and the food material.

9. The food composition as claimed in claim 7, wherein the compound selectively activates estrogen receptor β (ERβ) in menopause women.

* * * * *